United States Patent [19]

Inoki et al.

[11] Patent Number: 4,933,507
[45] Date of Patent: Jun. 12, 1990

[54] METHOD OF DEHYDROGENATING CYCLOHEXENONE

[75] Inventors: Satoshi Inoki; Yasushi Nakashima; Fujihisa Matsunaga, all of Ichihara, Japan

[73] Assignee: Mitsui Petrochemical Industries, Inc., Tokyo, Japan

[21] Appl. No.: 277,597

[22] Filed: Nov. 29, 1988

[30] Foreign Application Priority Data

Dec. 3, 1987 [JP] Japan .................. 62-306448

[51] Int. Cl.⁵ ............................ C07C 37/06
[52] U.S. Cl. ................................ 568/799
[58] Field of Search .............. 568/799, 835, 772

[56] References Cited

U.S. PATENT DOCUMENTS

| | | | |
|---|---|---|---|
| 2,503,641 | 4/1950 | Taylor et al. | 568/799 |
| 2,640,084 | 5/1953 | Chitwood et al. | 568/799 |
| 3,149,166 | 9/1964 | Poehler et al. | 568/361 |
| 3,256,348 | 6/1966 | Schlossman | 568/799 |
| 3,534,110 | 10/1970 | Jugun et al. | 568/799 |
| 3,801,651 | 4/1974 | Adolphen et al. | 568/799 |

FOREIGN PATENT DOCUMENTS

| | | | |
|---|---|---|---|
| 2107395 | 8/1977 | Fed. Rep. of Germany | 568/362 |
| 3314372 | 10/1984 | Fed. Rep. of Germany | 568/799 |
| 49-35365 | 4/1974 | Japan | 568/799 |
| 62-255443 | 11/1987 | Japan | 568/799 |
| 1162397 | 8/1969 | United Kingdom | 568/799 |

OTHER PUBLICATIONS

Article entitled: "Halogenation with Copper(II), II, Unsaturated Ketones" by Kosower and Wu; in J. Org. Chem., vol. 28, pp. 633–638. (1963).
Article entitled: "Nouvelle Methode D'Armoatisation de Cyclohexenones Contenues Dans des Systemes Polycycliques" by Bondon, Pietrasanta and Pucci in Tetrahedron Letters, No. 10, pp. 821–824, 1977.
Article entitled: "An Improved Method for the Preparation of 2-Cyclohexen-1-One by Sharma, Sethi and Dev, in Synthesie", pp. 45–46 (1974).
Article in J. Org. Chem., vol. 36, pp. 752–757, entitled "A New Method for the Preparation of $\alpha,\beta$-Unsaturated Carbonyl Compounds" by Theissen.

Primary Examiner—Werren B. Lone
Attorney, Agent, or Firm—Nixon & Vanderhye

[57] ABSTRACT

Phenol is produced by dehydrogenating cyclohexenone through a vapor-phase reaction in the presence hydrogen using a solid-phase catalyst having platinum and alkali metal carried on a support.

2 Claims, 1 Drawing Sheet

F I G. 1
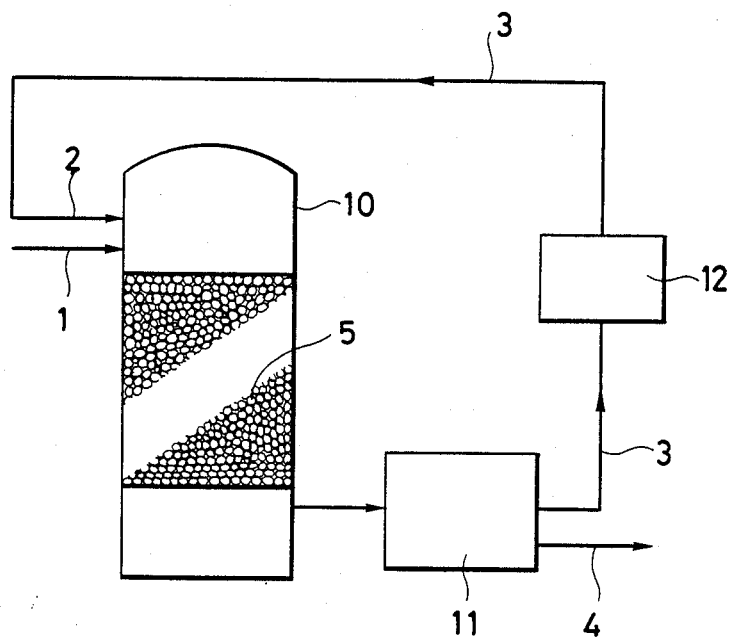

METHOD OF DEHYDROGENATING CYCLOHEXENONE

BACKGROUND OF THE INVENTION

The present invention relates to a novel method of dehydrogenating cyclohexenone, more particularly, to a method of phenol synthesis by vapor-phase reaction using a solid-phase catalyst.

Dehydrogenation reaction of cyclohexenone has conventionally been accomplished by the following methods: (1) cyclohexenone is reacted with $CuCl_2$ and LiCl to obtain phenol as described in J. Org. Chem., 28,633 (1963); and (2) cyclohexenone is reacted with $CuBr_2$ and LiCl to obtain phenol as described in Tetrahedron Lett., 821 (1977).

These methods are based on a liquid-phase reaction and require after-treatment including the removal of catalysts. In addition, $CuCl_2$ (or $CuBr_2$) has to be used in two moles per mole of cyclohexenone, whereas LiCl has to be used in a molar amount equal to that of cyclohexenone. Therefore, from the viewpoint of cost-effect-evenness, the methods are very difficult to practice on a commercial basis. As a further problem, the yield of phenol that can be obtained is in the range of 65–85%, which is far from being satisfactory.

SUMMARY OF THE INVENTION

An object, therefore, of the present invention is to solve the above-described problems of the prior art and to provide a novel method of dehydrogenating cyclohexenone by vapor-phase reaction using a solid-phase catalyst.

The object of the present invention can be attained by a method of dehydrogenating cyclohexenone wherein the reaction is performed in vapor phase in the presence of hydrogen using a solid-phase platinum/alkali metal catalyst on a support. Preferably, the catalyst support is silica, silica-alumina or alumina and the content of an alkali metal in the support is in the range of 0.5–2.0 wt % in terms of $Na_2O$.

The amount of platinum in the supported platinum/alkali metal catalyst is preferably in the range of 0.2–10 wt % of the sum of the support and the catalyst, and the amount of alkali metal in the catalyst is preferably in the range of 0.2–3.0 in terms of the weight ratio of $K_2CO_3$ to platinum.

Hydrogen is preferably supplied to the reaction system in a hydrogen-to-cyclohexenone molar ratio of 0.5–4.0.

BRIEF DESCRIPTION OF THE DRAWING

FIG. 1 is a diagram showing an example of the apparatus that can be used to implement the method of the present invention.

DETAILED DESCRIPTION OF THE INVENTION

The cyclohexenone to be dehydrogenated by the method of the present invention may contain other components such as cyclohexanone, cyclohexenol, cyclohexene oxide, etc.

Cyclohexenone can be readily synthesized by oxidizing cyclohexene with oxygen (or air) or by dehydrogenating cyclohexanone. A typical example of each method is described below:

(1) Oxidation of cyclohexene with oxygen (or air)

This method is described in Synthesis, 45 (1974), according to which cyclohexene is oxidized with oxygen with cobalt naphthenate used as a catalyst, and therefore treated with chromic acid to produce cyclohexenone in a yield of 80%;

(2) Dehydrogenation of cyclohexanone

This method is described in J. Org. Chem., 36,752 (1971), according to which cyclohexanone is dehydrogenated with both palladium chloride and copper chloride used as catalysts, to produce cyclohexenone at a selectivity of 90–95%.

The catalysts to be used in the method of the present invention may be of any type as long as it is a solid-phase catalyst having platinum and an alkali metal carried on a support.

The catalyst is preferably subjected to reduction or some other suitable treatment prior to starting a dehydrogenation reaction.

Dehydrogenation reaction of cyclohexenone using this catalyst is performed in vapor phase in the presence of hydrogen gas. In the absence of hydrogen gas, the intended dehydrogenation reaction will not proceed in an efficient way.

Hydrogen gas to be used may be pure hydrogen gas or a mixed gas containing an inert gas such as nitrogen gas. Recycling the hydrogen gas evolved as a by-product in the method of the present invention is preferred since it is advantageous from the viewpoints of economy and process efficiency.

In order to increase the yield of phenol which is the product of dehydrogenation of cyclohexenone, the following phenomena must be suppressed:

(1) formation of benzene;
(2) formation of tar due to the condensation of cyclohexenone; and
(3) formation of cyclohexanone and cyclohexanol which are hydrogenation products.

To meet this need, the method of the present invention is preferably performed under the following conditions.

(1) The catalyst is prepared by first treating a support with an aqueous solution of platinic acid, etc. to have platinum chloride carried on the support, then treating it to have an alkali metal compound such as $K_2CO_3$ supported thereon, and finally reducing the so treated support. Platinum is preferably supported in an amount of 0.2–10 wt %, more preferably 0.5–5 wt %, of the sum of the support and the catalysts. This range is selected from the viewpoints of catalyst activity and cost.

Examples of the alkali metal to be supported are Na and K, and their content is desirably in the range of 0.2–3.0 in terms of the weight of $K_2CO_3$ to platinum. This range is selected in order to avoid the increase in the amount of benzene which will occur as tar is produced on account of the condensation of cyclohexenone, and to avoid the decrease in the catalytic activity.

Details of the structure of the catalyst are unknown but it is speculated that platinum is supported in metallic form which is obtained by reduction whereas the alkali metal is supported in the form of a salt (e.g. $K_2CO_3$) or an oxide (e.g. $K_2O$).

(2) The catalyst support is preferably silica, silica-alumina or alumina. The content of alkali metal in the support is preferably in the range of 0.5–2.0 wt % in terms of $Na_2O$. This range assures minimum occurrence of benzene formation and cyclohexenone condensation.

(3) When cyclohexenone is allowed to pass through a column packed with the catalyst described above, hydrogen is also allowed to flow through the column simultaneously. Hydrogen is preferably supplied in an amount of 0.5-4.0 moles per mol of cyclohexenone supplied. If the molar ratio of hydrogen to cyclohexenone is 0.5 or more, the condensation reaction of cyclohexenone will take place only by a minimum degree. If the molar ratio of hydrogen to cyclohexenone is not more than 4.0, the formation of by-products (i.e., cyclohexanone and cyclohexanol which are hydrogenation products) is minimized, permitting easy purification of the reaction product by distillation.

(4) Cyclohexenone is preferably allowed to flow at an LHSV of 0.01-10 $hr^{-1}$, more preferably 0.1-5 $hr^{-1}$. If the flow rate of cyclohexenone is less than 0.01 $hr^{-1}$, the throughput is too small to justify commercial operations. If the flow rate of cyclohexenone is more than 10 $hr^{-1}$, conversion to phenol is undesirably low.

(5) The reaction temperature is preferably in the range of 300°-500° C., more preferably 350°-450° C. which assures the highest yield of phenol. If the reaction temperature is lower than 300° C., conversion to phenol is reduced. If the reaction temperature is higher than 500° C., an undesirably large amount of tar will be produced.

(6) The reaction pressure may be one atmosphere or of any value higher than it.

(7) The reaction apparatus for use in the practice of the method of the present invention may be exemplified but not limited to a continuous type as shown in FIG. 1.

The apparatus shown in FIG. 1 comprises a reactor 10 packed with a particulate catalyst 5 such as silica supporting a platinum/alkali metal catalyst, a phenol separator 11, an optional hydrogen gas scrubber 12, and piping 3 providing connection between these units. If desired, a hydrogen gas exhaust line (not shown in FIG. 1) is equipped in the piping 3. This exhaust line is equipped in order to draw out a part of hydrogen gas from this system. The reactor 10 has inlets in its upper part through which a feed gas 1 mainly composed of cyclohexenone and hydrogen 2 are to be supplied. It also has an outlet in its lower part through which the product gas obtained by dehydrogenation reaction of cyclohexenone is to be withdrawn.

The feed gas 1 and hydrogen gas 2 flow down through the reactor 10 while it is held at an appropriate temperature. The feed gas 1 is dehydrogenated by contact with the catalyst 5 and the dehydrogenated product enters the phenol separator 11 such as a distillation column, in which phenol 4 is separated and recovered from the reaction product. Hydrogen gas 2 is recycled to the reactor 10 through the piping 3. The hydrogen gas 2 being recycled may be subjected to a treatment such as scrubbing in the hydrogen gas scrubber 12.

If desired, a part of hydrogen gas is draw out from this system in order to balance the mole ratio of hydrogen to cyclohexenone properly.

The following examples are provided for the purpose of further illustrating the present invention but are in no way to be taken as limiting.

EXAMPLE 1

Hexachloroplatinic acid hexahydrate (1.08 g) was dissolved in 60 ml of ion-exchanged water. To the solution, 40 g of a silica support containing 1.0% $Na_2O$ was added and the mixture was left to stand for 12 hours at room temperature after stirring for 2 hours. The mixture was dehydrated with an evaporator and dried with an electric heater at 110° C. for 12 hours.

In a separate step, 0.20 g of potassium carbonate was dissolved in 40 ml of a mixed solvent consisting of 30% acetone and 70% water. The previously prepared catalyst was added to the solution and the mixture was left to stand for 12 hours at room temperature after stirring for 2 hours. The mixture was dehydrated with an evaporator and dried with an electric heater at 110° C. for 12 hours. The resulting catalyst contained 0.9 wt % Pt and 0.5 wt % $K_2CO_3$ on the basis of silica weight.

A steel reactor for use in the flow method was packed with 20 ml of the Pt/$K_2CO_3$ catalyst on silica and subsequently supplied with hydrogen at a rate of ca. 10 l/hr to perform a dehydrogenation treatment at 400° C. for 10 hours.

Thereafter, cyclohexenone was passed through the reactor at an LHSV of 0.5 $hr^{-1}$, a reaction temperature of 400° C. and at an atmospheric reaction pressure, with the molar ratio of hydrogen to cyclohexenone being held at 2 at the entrance of the reactor.

The product obtained at the exit end of the reactor was analyzed quantitatively by gas chromatography. The reaction solution was found to have the following composition:

| Components | Mole % |
|---|---|
| Phenol | 97.4 |
| Cyclohexanol | 0.1 |
| Cyclohexanone | 0.7 |
| Benzene | 1.8 |
| Others | 0.1 |

EXAMPLE 2

Cyclohexenone was dehydrogenated under the same reaction conditions as those employed in Example 1 except that the catalyst was prepared with the amount of $K_2CO_3$ changed from 0.20 g to 0.80 g. The resulting catalyst consisted of 0.9 wt % Pt and 2.0 wt % $K_2CO_3$ based on silica weight. The reaction solution obtained had the following composition:

| Components | Mole % |
|---|---|
| Phenol | 96.8 |
| Cyclohexanol | 0.1 |
| Cyclohexanone | 1.5 |
| Benzene | 1.2 |
| Cyclohexenone | 0.1 |
| Others | 0.3 |

EXAMPLE 3

Using the catalyst prepared in Example 1, cyclohexenone was dehydrogenated under the same reaction conditions as those employed in Example 1 except that the reaction temperature was changed to 390° C. and hydrogen/cyclohexenone molar ratio to 0.5. The reaction solution obtained had the following composition:

| Components | Mole % |
|---|---|
| Phenol | 96.2 |
| Cyclohexanol | 0.1 |
| Cyclohexanone | 0.6 |
| Benzene | 2.5 |

| Components | Mole % |
|---|---|
| Cyclohexenone | 0.1 |
| Others | 0.5 |

EXAMPLE 4

Using the catalyst prepared in Example 1, cyclohexenone was dehydrogenated under the same reaction conditions as those employed in Example 1 except that the reaction temperature was changed to 410° C. and the hydrogen/cyclohexenone molar ratio to 4.0. The reaction solution obtained had the following composition:

| Components | Mole % |
|---|---|
| Phenol | 96.4 |
| Cyclohexanol | 0.1 |
| Cyclohexanone | 0.3 |
| Benzene | 3.0 |
| Others | 0.2 |

COMPARATIVE EXAMPLE 1

Cyclohexenone was dehydrogenated under the same reaction conditions as those employed in Example 1 using the same catalyst as that prepared in Example 1 except that potassium was not supported.

The reaction solution obtained had the following composition, which apparently shows an increase in the formation of benzene and tar and a decrease in the yield of phenol.

| Components | Mole % |
|---|---|
| Phenol | 86.3 |
| Cyclohexanol | 0.1 |
| Cyclohexanone | 4.8 |
| Benzene | 3.5 |
| Cyclohexenone | 0.3 |
| Others (including tar) | 5.0 |

The present invention provides a method of dehydrogenating cyclohexenone in vapor phase using a solid-phase catalyst and offers the following advantages:

(1) since it is a vapor-phase method, it does not require an after-treatment such as catalyst recovery;
(2) since the reaction proceeds by catalytic action, the production cost, in particular the materials cost, is low; and
(3) the yield of phenol is high.

What is claimed is:

1. A method of dehydrogenating cyclohexenone to phenol comprising reacting in the vapor phase hydrogen and cyclohexenone in a molar ratio of 0.5 to 4.0 moles of hydrogen per mole of cyclohexenone at a pressure of at least one atmosphere and a reaction temperature of 300° C. to 500° C. using a solid phase catalyst containing platinum, in the range of 0.2 to 10 wt % of the sum of the catalyst plus support, and an alkali metal, in the range of 0.2 to 3.0 calculated in terms of the weight ratio of $K_2CO_3$ to platinum, both the platinum and the alkali metal carried on a support.

2. A method according to claim 1 wherein the catalyst support is silica, silica-alumina or alumina, and the content of an alkali metal in the catalyst support is in the range of 0.5–2.0 wt % in terms of $Na_2O$.

* * * * *